(12) United States Patent
She et al.

(10) Patent No.: US 11,650,194 B2
(45) Date of Patent: May 16, 2023

(54) DYNAMIC DAMAGE EVALUATION INSTRUMENT OF DRILLING FLUID BASED ON GLASS CORE

(71) Applicant: Chengdu University of Technology, Chengdu (CN)

(72) Inventors: Jiping She, Chengdu (CN); Hao Zhang, Chengdu (CN); Bin Yang, Chengdu (CN); Yang Yang, Chengdu (CN); Yang Li, Chengdu (CN); Jianjun Ni, Chengdu (CN); Gege Teng, Chengdu (CN); Ying Zhong, Chengdu (CN)

(73) Assignee: Chengdu University of Technology, Chengdu (CN)

( * ) Notice: Subject to any disclaimer, the term of this patent is extended or adjusted under 35 U.S.C. 154(b) by 0 days.

(21) Appl. No.: 17/647,599

(22) Filed: Jan. 11, 2022

(65) Prior Publication Data

US 2022/0229039 A1 Jul. 21, 2022

(30) Foreign Application Priority Data

Jan. 15, 2021 (CN) .......................... 202110051462.6

(51) Int. Cl.
*G01N 33/28* (2006.01)
*G01N 1/38* (2006.01)

(52) U.S. Cl.
CPC ........... *G01N 33/2823* (2013.01); *G01N 1/38* (2013.01)

(58) Field of Classification Search
CPC ............................ G01N 33/2823; G01N 1/38
See application file for complete search history.

(56) References Cited

FOREIGN PATENT DOCUMENTS

| CN | 203961858 U | * | 11/2014 | |
|---|---|---|---|---|
| CN | 104747187 A | * | 7/2015 | |
| CN | 111337411 A | * | 6/2020 | |
| CN | 210863452 U | * | 6/2020 | |
| CN | 112540036 A | * | 3/2021 | ......... G01N 15/0806 |

OTHER PUBLICATIONS

English abstract CN104747187 from worldwide.espacenet.com, accessed Nov. 17, 2022.*

(Continued)

*Primary Examiner* — David Z Huang
*Assistant Examiner* — Jean F Morello
(74) *Attorney, Agent, or Firm* — Bayramoglu Law Offices LLC

(57) ABSTRACT

A dynamic damage evaluation instrument of drilling fluid based on a glass core includes a controller and a support. A kettle body is provided on the support, a well for receiving drilling fluid is provided inside the kettle body, and a well cover is provided at an upper end of the kettle body. A core holding assembly communicating with the well is provided at a side of the kettle body, and a metering assembly is movably provided at the other end of the core holding assembly. A stirrer for stirring drilling fluid is provided inside the well, and a power component for driving the stirrer is provided outside the kettle body. A data detection hole for mounting a temperature and pressure sensor and a pressurization hole for mounting a pressurization device are formed on the well cover.

10 Claims, 4 Drawing Sheets

(56) References Cited

OTHER PUBLICATIONS

English abstract CN112540036 from worldwide.espacenet.com, accessed Nov. 17, 2022.*
English abstract CN111337411 from worldwide.espacenet.com, accessed Nov. 17, 2022.*
English abstract CN210863452 from worldwide.espacenet.com, accessed Nov. 17, 2022.*
English abstract for CN203961858 accessed from worldwide.espacenet.com Nov. 17, 2022.*

* cited by examiner

DYNAMIC DAMAGE EVALUATION INSTRUMENT OF DRILLING FLUID BASED ON GLASS CORE

CROSS REFERENCE TO THE RELATED APPLICATIONS

This application is based upon and claims priority to Chinese Patent Application No. 202110051462.6, filed on Jan. 15, 2021, the entire contents of which are incorporated herein by reference.

TECHNICAL FIELD

The present invention relates to the field of drilling exploration, and more particularly, to a dynamic damage evaluation instrument of drilling fluid based on a glass core.

BACKGROUND

Lost circulation is one of the most troublesome drilling problems. The loss of costly drilling fluid into the stratum results in an increased economic cost and may also lead to some well control problems. About 20% to 25% of all wells worldwide undergo lost circulation, and thus lost circulation has always been a concern in and outside China.

Fluid loss refers to the permeation of free water in drilling fluid into cracks or pores of the well wall rock under the action of a pressure difference. In a fluid loss process, some solid particles in drilling fluid adhere to a well wall to form a mud cake, and the mud cake formed on the well wall will prevent or slow down the further permeation of water in the drilling fluid into the stratum. In order to maintain the stability of a borehole and reduce the penetration of solid and liquid phases of drilling fluid into the stratum, it is necessary to control the fluid loss performance of the drilling fluid. Therefore, how to correctly evaluate the leaking stoppage effect for drilling fluid in the laboratory research and establish a dynamic damage measurement method of the drilling fluid is of great significance for avoiding lost circulation and protecting the reservoir. In the prior indoor dynamic damage evaluation instrument of drilling fluid, a fluid loss of the drilling fluid is determined by receiving the drilling fluid flowing out from a core port through an adjusting rod (a guide rod) and a container, the adjusting rod is usually arranged horizontally, and the entire evaluation instrument is heavy and difficult to tilt. Therefore, in this manner, a part of the drilling fluid flowing out from the core port will remain in gaps in the adjusting rod, and an amount of the drilling fluid remaining is large because the adjusting rod usually has a length of more than 10 cm, making it impossible to accurately measure the fluid loss of the drilling fluid and thus it impossible to accurately evaluate the damage of the drilling fluid.

In addition, because there is a high pressure in a well of the evaluation instrument and the prior direct connection to drive a stirrer cannot meet the high pressure sealing requirements, the air drive of a magnetic coupling is usually adopted. However, the magnetic coupling has a low torque under the high pressure in the well, which makes the rotational speed of the stirrer difficult to meet high simulation requirements; and the rotational speed of the stirrer cannot be measured in a high pressure environment, making the drilling fluid difficult to reach an expected shear rate. Moreover, most of the prior core holders are made of stainless steel without a visualized design, and thus users cannot know the status of the core in use.

SUMMARY

In view of the above-mentioned shortcomings in the art, the present invention provides a dynamic damage evaluation instrument of drilling fluid based on a glass core, which solves the problem that the existing evaluation instrument cannot accurately evaluate the damage of drilling fluid.

In order to achieve the above objective, the present invention adopts the following technical solutions:

A dynamic damage evaluation instrument of drilling fluid based on a glass core is provided, including a controller and a support, where a kettle body is provided on the support, a well for receiving drilling fluid is provided inside the kettle body, and a well cover is provided at an upper end of the kettle body; a core holding assembly communicating with the well is provided at a side of the kettle body, and a metering assembly is movably provided at the other end of the core holding assembly; a stirrer for stirring drilling fluid is provided inside the well, and a power component for driving the stirrer is provided outside the kettle body; a data detection hole for mounting a temperature and pressure sensor and a pressurization hole for mounting a pressurization device are formed on the well cover;

the metering assembly includes a guide rod, a guide chamber penetrating one end of the guide rod is provided inside the guide rod, and a piston is provided inside the guide chamber; a liquid inlet and a liquid outlet connected to a side of the guide rod are formed at an end of the guide chamber; the liquid inlet is connected to a liquid supply device, and a first valve is provided between the liquid inlet and the liquid supply device; the liquid outlet is connected to a container, and a second valve is provided between the liquid outlet and the container;

the core holding assembly includes a housing, and a first chamber for holding the glass core and a second chamber for connecting the metering assembly are formed inside the housing; the first chamber and the second chamber are connected to penetrate the housing; a light source and a temperature sensor are embedded on an inner wall of the first chamber, and the housing is provided with a first window penetrating to the first chamber; a diameter of the first chamber is larger than a diameter of the second chamber; and the power component, the temperature and pressure sensor, the pressurization device, the light source, and the temperature sensor are connected to the controller, respectively.

Further, a flow meter may be provided between the liquid outlet and the container, and the flow meter may be connected to the controller.

Further, a first bolt hole may be formed on an upper end surface of the kettle body, a second bolt hole corresponding to the first bolt hole may be formed on the well cover, and the kettle body and the well cover may be connected by a bolt.

Further, a second window may be provided on a side wall of the kettle body, and both the first window and the second window may be pressure-resistant glass.

Further, the power component may include a motor and a magnetic coupling connected to a rotating shaft of the motor, and the magnetic coupling may be arranged at a bottom of the kettle body; a permanent magnet matched with the magnetic coupling may be provided at a bottom of the stirrer; and the motor may be connected to the controller.

Further, the power component may include a winding arranged on a side wall of the kettle body, and a protective cover may be provided outside the winding; a permanent magnet matched with a magnetic field generated by the winding when energized may be provided at a side of the stirrer; and the winding may be connected to the controller.

Further, an electric heating wire may be provided on the housing, and the electric heating wire may be connected to the controller.

Further, the guide rod may include a thread section and a limit section; threads matched with each other may be respectively formed on an outer surface of the thread section and an inner surface of the first chamber; a diameter of the limit section may be identical to the diameter of the second chamber; and a diameter of the thread section may be larger than the diameter of the limit section.

Further, a first sealing ring may be provided at a front end of the limit section, and a second sealing ring may be provided at a front end of the thread section.

Further, a stopper may be provided in the end of the guide chamber adjacent to the liquid inlet or the liquid outlet.

The present invention has the following beneficial effects:

1. In the present invention, the guide chamber is first filled with drilling fluid through the liquid inlet, such that the piston is in close contact with the glass core; with the guide chamber being full of the drilling fluid, an end connected to the container is arranged to be higher than the first valve; the second valve is opened, such that the drilling fluid fills a pipeline from the first valve to the container; then the first valve is closed, such that the drilling fluid reaches a specified position in the well; the well cover is covered, and the temperature and pressure sensor and the pressurization device are connected to the corresponding holes on the well cover; the pressurization device is started to pressurize the well, the power component is started to drive the stirrer, and the received drilling fluid is recorded through the container until no drilling fluid flows into the container, thereby acquiring a fluid loss of the drilling fluid and completing the damage evaluation of the drilling fluid. The evaluation instrument can prevent drilling fluid from remaining in a guide chamber and can also count drilling fluid filled in the glass core, which can greatly improve the estimation accuracy of a fluid loss of the drilling fluid, thereby improving the accuracy of damage evaluation of the drilling fluid.

2. Through the first window of the evaluation instrument, the status of the glass core in use can be observed, which facilitates a user to directly understand the process that core gaps are plugged by drilling fluid, and increases the understanding of plugging of drilling fluid in gaps.

3. In the arrangement mode where the second chamber is larger than the first chamber, a depth of the guide rod entering the core holding assembly can be flexibly adjusted, and thus the support for the glass core can be flexibly adjusted, such that end surfaces of glass cores with different lengths can be flush with an inner wall of a well, which increases the flexibility of test subject selection.

4. The temperature sensor can acquire a temperature of the glass core in real time, which facilitates a user to understand a status of the glass core and thus accurately simulate the underground environment.

5. With the second window, a user can easily observe a status inside a well and a flow status of drilling fluid inside a well to indirectly obtain a rotational speed of the stirrer, which facilitates a user to adjust the power component to enable an appropriate rotational speed, making drilling fluid reach an expected shear rate.

6. In the present invention, a strong magnetic field is generated by the winding to drive the stirrer, and a size and a direction of the magnetic field can be adjusted to drive and adjust the rotational speed, which can provide a greater stirring torque than the magnetic coupling, and enables the evaluation instrument to adapt to higher simulation requirements.

7. The electric heating wire can heat the glass core and drilling fluid in the glass core to simulate a temperature environment in a true well, thereby improving the evaluation accuracy.

8. The guide rod is arranged in two sections, such that a length of the limit section can be flexibly selected to adapt to glass cores with different lengths, which improves the practicability.

9. The first sealing ring and the second sealing ring can prevent drilling fluid from entering gaps between the guide rod and the housing to improve the evaluation accuracy, and can also avoid the hard contact between a head end of the thread section and the first chamber and between a head end of the limit section and the glass core to improve the durability of the evaluation instrument.

10. The stopper can prevent the piston from moving to the liquid inlet or the liquid outlet, thereby preventing the piston from affecting the filling of drilling fluid in the guide chamber and improving the use convenience of the evaluation instrument.

11. The flow meter allows the controller to directly read a fluid loss of drilling fluid, and can also correct the fluid loss obtained through the container, thereby improving the evaluation accuracy.

Figure 1:
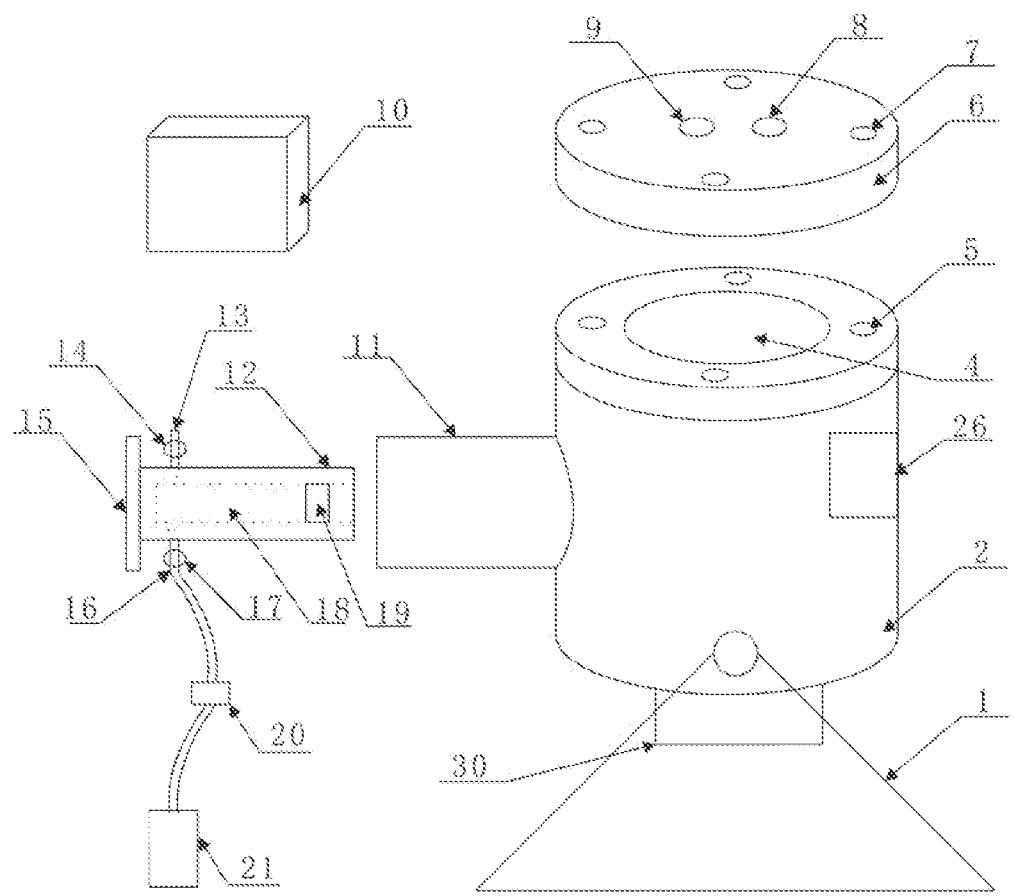
FIG. 1 is a schematic structural diagram of the evaluation instrument driven by a motor.

In the figures: 1 represents a support; 2 represents a kettle body; 3 represents a protective cover; 4 represents a well; 5 represents a first bolt hole; 6 represents a well cover; 7 represents a second bolt hole; 8 represents a data detection hole; 9 represents a pressurization hole; 10 represents a controller; 11 represents a core holding assembly; 12 represents a guide rod; 13 represents a liquid inlet; 14 represents a first valve; 15 represents a handle; 16 represents a liquid outlet; 17 represents a second valve; 18 represents a guide chamber; 19 represents a piston; 20 represents a flow meter; 21 represents a container; 22 represents a winding; 23 represents a glass core; 24 represents a light source; 25 represents a first window; 26 represents a second window; 27 represents a temperature sensor; 28 represents an electric heating wire; 29 represents a housing; 30 represents a motor; 31 represents a first chamber; 32 represents a second chamber; 33 represents a stopper; 34 represents a thread section; 35 represents a limit section; 36 represents a first sealing ring; and 37 represents a second sealing ring.

DETAILED DESCRIPTION OF THE EMBODIMENTS

Specific implementations of the present invention are described below to facilitate those skilled in the art to understand the present invention, but it should be known that the present invention is not limited to the scope of the specific implementations. For those of ordinary skill in the art, as long as various changes are within the spirit and scope of the present invention that are defined and determined by the attached claims, these changes are obvious, and all innovations using the concept of the present invention are protected.

As shown in FIG. 1, FIG. 2, FIG. 3, FIG. 4, and FIG. 5, the dynamic damage evaluation instrument of drilling fluid based on a glass core includes a controller 10 and a support 1, where a kettle body 2 is provided on the support 1, a well 4 for receiving drilling fluid is provided inside the kettle body 2, and a well cover 6 is provided at an upper end of the kettle body 2; a core holding assembly 11 communicating with the well 4 is provided at a side of the kettle body 2, and a metering assembly is movably provided at the other end of the core holding assembly 11; a stirrer for stirring drilling fluid is provided inside the well 4, and a power component for driving the stirrer is provided outside the kettle body 2; a data detection hole 8 for mounting a temperature and pressure sensor and a pressurization hole 9 for mounting a pressurization device are formed on the well cover 6;

the metering assembly includes a guide rod 12, a guide chamber 18 penetrating one end of the guide rod 12 is provided inside the guide rod 12, and a piston 19 is provided inside the guide chamber 18; a liquid inlet 13 and a liquid outlet 16 connected to a side of the guide rod 12 are formed at an end of the guide chamber 18; the liquid inlet 13 is connected to a liquid supply device, and a first valve 14 is provided between the liquid inlet 13 and the liquid supply device; the liquid outlet 16 is connected to a container 21, and a second valve 17 is provided between the liquid outlet 16 and the container 21;

the core holding assembly 11 includes a housing 29, and a first chamber 31 for holding the glass core 23 and a second chamber 32 for connecting the metering assembly are formed inside the housing 29; the first chamber 31 and the second chamber 32 are connected to penetrate the housing 29; a light source 24 and a temperature sensor 27 are embedded on an inner wall of the first chamber 31, and the housing 29 is provided with a first window 25 penetrating to the first chamber 31; a diameter of the first chamber 31 is larger than a diameter of the second chamber 32; and the power component, the temperature and pressure sensor, the pressurization device, the light source 24, and the temperature sensor 27 are connected to the controller 10, respectively.

In order to enable the controller 10 to directly read a fluid loss of drilling fluid and correct the fluid loss obtained through the container 21 to improve the evaluation accuracy, a flow meter 20 may be provided between the liquid outlet 16 and the container 21, and the flow meter 20 may be connected to the controller 10.

In order to facilitate the disassembly of the well cover 6, a first bolt hole 5 may be formed on an upper end surface of the kettle body 2, a second bolt hole 7 corresponding to the first bolt hole 5 may be formed on the well cover 6, and the kettle body 2 and the well cover 6 may be connected by a bolt.

In order to facilitate a user to observe a status inside a well 4 and a flow status of drilling fluid inside a well 4 to indirectly obtain a rotational speed of the stirrer and facilitate a user to adjust the power component to enable an appropriate rotational speed and make drilling fluid reach an expected shear rate, a second window 26 may be provided on a side wall of the kettle body 2, and both the first window 25 and the second window 26 may be pressure-resistant glass.

Figure 2:
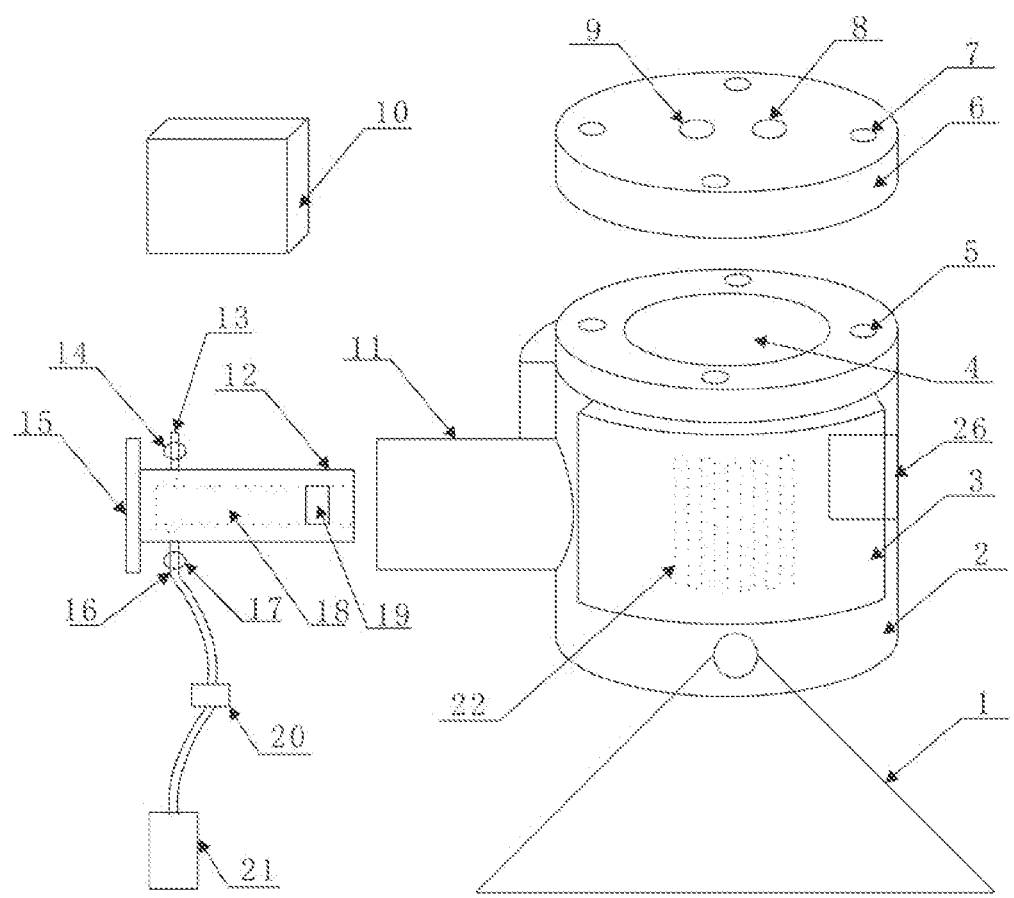
FIG. 2 is a schematic structural diagram of the evaluation instrument driven by a winding.

As shown in FIG. 2, the power component may include a motor 30 and a magnetic coupling connected to a rotating shaft of the motor, and the magnetic coupling may be arranged at a bottom of the kettle body 2; a permanent magnet matched with the magnetic coupling may be provided at a bottom of the stirrer; and the motor 30 may be connected to the controller 10.

In order to generate a strong magnetic field to drive the stirrer, drive and adjust the rotational speed by adjusting a size and a direction of the magnetic field, provide a greater stirring torque than the magnetic coupling, and enable the evaluation instrument to adapt to higher simulation requirements, the power component may include a winding 22 arranged on a side wall of the kettle body 2, and a protective cover 3 may be provided outside the winding 22; a permanent magnet matched with a magnetic field generated by the winding 22 when energized may be provided at a side of the stirrer; and the winding 22 may be connected to the controller 10.

Figure 3:
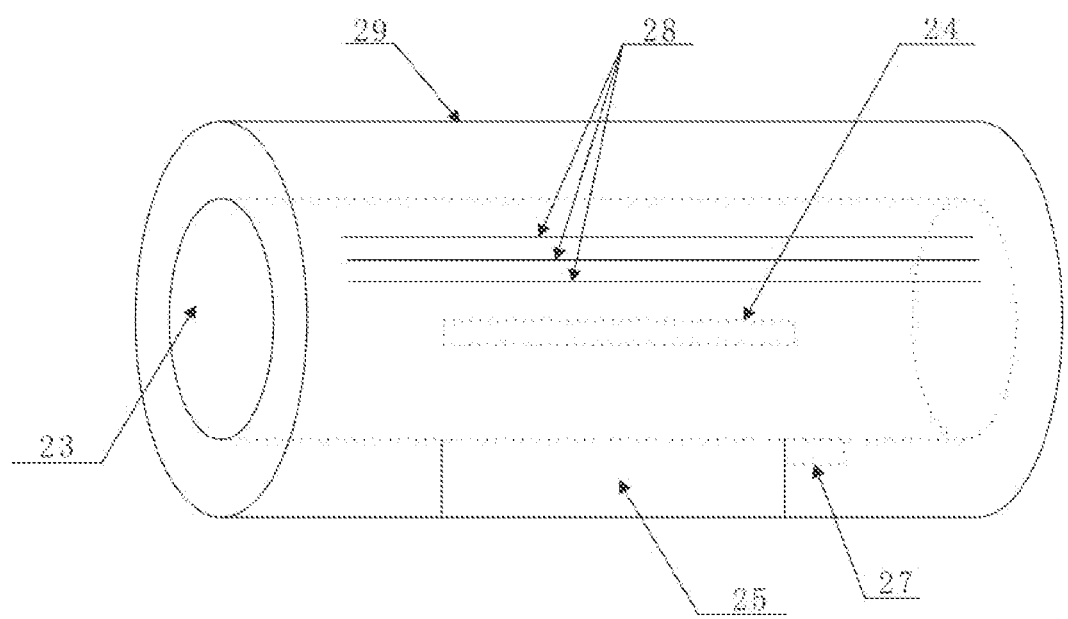
FIG. 3 is a schematic structural diagram of the core holding assembly.

As shown in FIG. 3, in order to heat the glass core 23 and drilling fluid in the glass core 23 to simulate a temperature environment in a true well 4 and improve the evaluation accuracy, an electric heating wire 28 may be provided on the housing 29, and the electric heating wire 28 may be connected to the controller 10.

Figure 4:
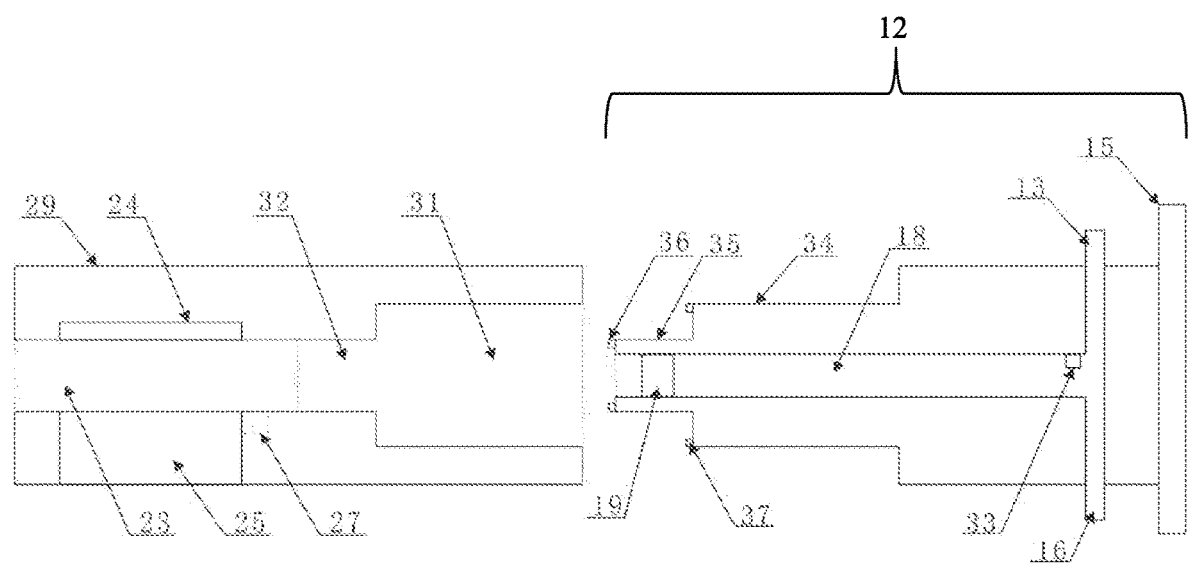
FIG. 4 is a cross-sectional view of the core holding assembly and the guide rod.
Figure 5:
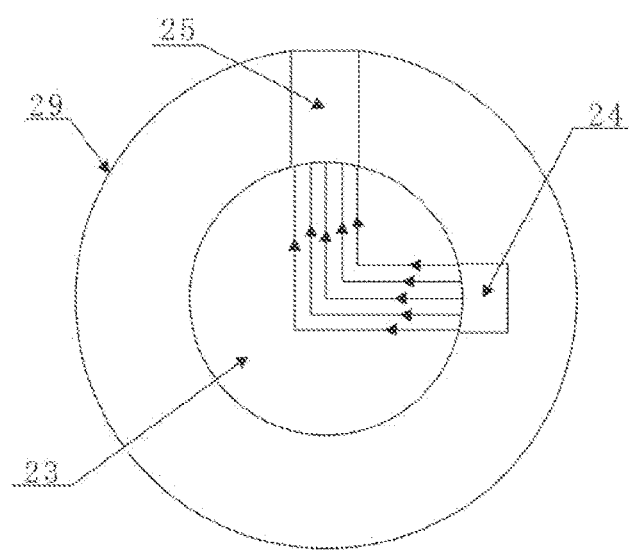
FIG. 5 is a schematic cross-sectional view of the core holding assembly at the light source.

As shown in FIG. 4, in order to flexibly select a length of the limit section 35 to adapt to glass cores 23 with different lengths and improve the practicability, the guide rod 12 may include a thread section 34 and a limit section 35; threads may be respectively formed on an outer surface of the thread section 34 and an inner surface of the first chamber 31; a diameter of the limit section 35 may be identical to the diameter of the second chamber 32; and a diameter of the thread section 34 may be larger than the diameter of the limit section 35. A handle 15 may also be provided at a tail end of the guide rod 12 to facilitate assembly and disassembly.

In order to prevent drilling fluid from entering gaps between the guide rod 12 and the housing 29 to improve the evaluation accuracy and avoid the hard contact between a head end of the thread section 34 and the first chamber 31 and between a head end of the limit section 35 and the glass core 23 to improve the durability of the evaluation instrument, a first sealing ring 36 may be provided at a front end of the limit section 35, and a second sealing ring 37 may be provided at a front end of the thread section 34.

In order to prevent the piston 19 from moving to the liquid inlet 13 or the liquid outlet 16 to prevent the piston 19 from affecting the filling of drilling fluid in the guide chamber 18 and improve the use convenience of the evaluation instrument, a stopper 33 may be provided in the end of the guide chamber 18 adjacent to the liquid inlet 13 or the liquid outlet 16.

In an embodiment of the present invention, a use process of the evaluation instrument may include the following steps:

S1. the glass core 23 is put into the second chamber 32, and the end surface of the glass core 23 is allowed to be flush with the inner wall of the well 4;

S2. the guide rod 12 is screwed into the housing 29, the second valve 17 is closed, and the first valve 14 is opened, such that the drilling fluid in the liquid supply device flows into the guide chamber 18, and the gas between the piston 19 and the glass core 23 is discharged through gaps of the glass core 23;

S3. the guide chamber 18 is filled such that the piston 19 is in close contact with the glass core 23, and an end connected to the container 21 is arranged to be higher than the first valve 14 to prevent the drilling fluid in the pipeline from flowing out naturally;

S4. the second valve 17 is opened such that the drilling fluid fills the pipeline between the first valve 14 and the container 21;

S5. the first valve 14 is closed, such that the drilling fluid reaches a specified position (height) in the well 4; and then the well cover 6 is covered, and the temperature and pressure sensor and the pressurization device are connected to the corresponding holes on the well cover 6;

S6. the pressurization device is started to pressurize the well 4, the power component is started to drive the stirrer, and the received liquid is recorded through the container 21 and the flow meter 20 until no fluid flows into the container 21; and S7. a fluid loss of the drilling fluid is acquired according to a fluid volume recorded by the container 21 and the flow meter 20 to complete the damage evaluation of the drilling fluid.

In use, a user can observe a status of the glass core 23 in use through the first window 25, which facilitates a user to directly understand the process that core gaps are plugged by drilling fluid, and increases the understanding of plugging of drilling fluid in gaps. A user can also heat the glass core 23 through the electric heating wire 28, a temperature of the glass core 23 can be obtained through the temperature sensor 27, a temperature and a pressure in the well 4 can be obtained through the temperature and pressure sensor, and a pressure in well 4 and a rotational speed of the stirrer can be adjusted by adjusting the pressurization device and power component.

In a specific implementation process, the light source 24 can be embedded as follows: a window is arranged and a light source 24 is arranged outside the window.

In summary, the present invention can prevent drilling fluid from remaining in the guide chamber 18 and count drilling fluid filled in the glass core 23, which can greatly improve the estimation accuracy of a fluid loss of the drilling fluid, thereby improving the accuracy of damage evaluation of the drilling fluid.

What is claimed is:

1. A dynamic damage evaluation instrument of drilling fluid based on a glass core, comprising a controller and a support, wherein a kettle body is provided on the support, a well for receiving the drilling fluid is provided inside the kettle body, and a well cover is provided at an upper end of the kettle body; a first end of a core holding assembly communicating with the well is provided at a side of the kettle body, and a metering assembly is movably provided at a second end of the core holding assembly; a stirrer for stirring the drilling fluid is provided inside the well, and a power component for driving the stirrer is provided outside the kettle body; a data detection hole for mounting a temperature and pressure sensor and a pressurization hole for mounting a pressurization device are formed on the well cover;

the metering assembly comprises a guide rod, a guide chamber penetrating one end of the guide rod is provided inside the guide rod, and a piston is provided inside the guide chamber; a liquid inlet and a liquid outlet are formed at an end of the guide chamber, wherein the liquid inlet and the liquid outlet are connected to a side of the guide rod; the liquid inlet is connected to a liquid supply device, and a first valve is provided between the liquid inlet and the liquid supply device; the liquid outlet is connected to a container, and a second valve is provided between the liquid outlet and the container;

the core holding assembly comprises a housing, and a first chamber for holding the glass core and a second chamber for connecting the metering assembly are formed inside the housing; the first chamber and the second chamber are connected to penetrate the housing; a light source and a temperature sensor are embedded on an inner wall of the first chamber, and the housing is provided with a first window penetrating to the first chamber; a diameter of the first chamber is larger than a diameter of the second chamber; and the power component, the temperature and pressure sensor, the pressurization device, the light source, and the temperature sensor are connected to the controller, respectively.

2. The dynamic damage evaluation instrument of the drilling fluid based on the glass core according to claim 1, wherein a flow meter is provided between the liquid outlet and the container, and the flow meter is connected to the controller.

3. The dynamic damage evaluation instrument of the drilling fluid based on the glass core according to claim 1, wherein a first bolt hole is formed on an upper end surface of the kettle body, a second bolt hole corresponding to the first bolt hole is formed on the well cover, and the kettle body and the well cover are connected by a bolt.

4. The dynamic damage evaluation instrument of the drilling fluid based on the glass core according to claim 1, wherein a second window is provided on a side wall of the kettle body, and the first window and the second window are pressure-resistant glass.

5. The dynamic damage evaluation instrument of the drilling fluid based on the glass core according to claim 1, wherein the power component comprises a motor and a magnetic coupling connected to a rotating shaft of the motor, and the magnetic coupling is arranged at a bottom of the kettle body; a permanent magnet matched with the magnetic coupling is provided at a bottom of the stirrer; and the motor is connected to the controller.

6. The dynamic damage evaluation instrument of the drilling fluid based on the glass core according to claim 1, wherein the power component comprises a winding arranged on a side wall of the kettle body, and a protective cover is provided outside the winding; a permanent magnet matched with a magnetic field generated by the winding when energized is provided at a side of the stirrer; and the winding is connected to the controller.

7. The dynamic damage evaluation instrument of the drilling fluid based on the glass core according to claim 1, wherein an electric heating wire is provided on the housing, and the electric heating wire is connected to the controller.

8. The dynamic damage evaluation instrument of the drilling fluid based on the glass core according to claim 1, wherein the guide rod comprises a thread section and a limit section; threads matched with each other are respectively formed on an outer surface of the thread section and an inner surface of the first chamber; a diameter of the limit section is identical to the diameter of the second chamber; and a diameter of the thread section is larger than the diameter of the limit section.

9. The dynamic damage evaluation instrument of the drilling fluid based on the glass core according to claim 8, wherein a first sealing ring is provided at a front end of the limit section, and a second sealing ring is provided at a front end of the thread section.

10. The dynamic damage evaluation instrument of the drilling fluid based on the glass core according to claim 1, wherein a stopper is provided in the end of the guide chamber, wherein the end of the guide chamber is adjacent to the liquid inlet or the liquid outlet.

* * * * *